US00PP23593P3

(12) United States Plant Patent
Bañados et al.

(10) Patent No.: US PP23,593 P3
(45) Date of Patent: May 14, 2013

(54) RASPBERRY PLANT NAMED 'PACIFIC MAJESTY'

(50) Latin Name: *Rubus idaeus*
Varietal Denomination: Pacific Majesty

(75) Inventors: Pilar Bañados, Huechuraba (CL); A. Ellen Thompson, Fayetteville, AR (US); Miguel Alliende, Huechuraba (CL); Victor Moller, Huechuraba (CL); John R. Clark, Fayetteville, AR (US)

(73) Assignee: Pacific Berry Breeding, LLC, Salinas, CA (US)

( * ) Notice: Subject to any disclaimer, the term of this patent is extended or adjusted under 35 U.S.C. 154(b) by 0 days.

(21) Appl. No.: 13/136,977

(22) Filed: Aug. 15, 2011

(65) Prior Publication Data

US 2013/0047306 P1 Feb. 21, 2013

(51) Int. Cl.
*A01H 5/00* (2006.01)

(52) U.S. Cl.
USPC ..... Plt./204

(58) Field of Classification Search ..... Plt./204
See application file for complete search history.

(56) References Cited

U.S. PATENT DOCUMENTS

| | | | |
|---|---|---|---|
| PP17,819 | P3 | 6/2007 | Jennings |
| PP19,512 | P3 | 12/2008 | Hauenstein |
| PP21,536 | P3 | 11/2010 | Amrhein et al. |

*Primary Examiner* — Annette Para
(74) *Attorney, Agent, or Firm* — Graybeal Jackson LLP

(57) ABSTRACT

A new and distinct cultivar of Raspberry plant named 'Pacific Majesty' as described and shown herein. 'Pacific Majesty' provides typically larger fruit, better firmness and typically higher yields than 'Rafzaqu', U.S. Plant Pat. No. 19,512 and 'Marcela' U.S. Plant Pat. No. 17,819. 'Pacific Majesty' provides fruit with a lighter red color than 'Pacifci Royale' U.S. Plant Pat. No. 21,536. Distinct characteristics of 'Pacific Majesty' include the combination of very large, conic fruit, bright color and high yield.

4 Drawing Sheets

BACKGROUND AND SUMMARY

Raspberries are a well-known, aggregate fruit grown commercially throughout the world. One example of an existing, patented raspberry variety is 'Rafzaqu' (marketed as 'Himbo-Top'®), U.S. Plant Pat. No. 19,512. Another example of an existing, patented raspberry variety is 'Pacific Royale', U.S. Plant Pat. No. 21,536. A third example of an existing, patented variety is 'Marcela', U.S. Plant Pat. No. 17,819. Such varieties, however, do not provide large enough fruit, yield enough, or produce berries with bright enough color to be competitive in the commercial market. Thus, there is a need for raspberry varieties that provide larger fruit, brighter color, higher yields and that are competitive.

The present cultivar, 'Pacific Majesty', provides one or more of these, or other characteristics. For example, the present cultivar, 'Pacific Majesty', provides typically larger fruit than 'Rafzaqu' and 'Marcela'. Further, 'Pacific Majesty' produces berries that are larger and of lighter red color as compared to 'Pacific Royale'. 'Pacific Majesty' also produces higher yields than 'Rafzaqu', 'Pacific Royale', and 'Marcela'. The fruits of 'Pacific Majesty' are also firmer than those of 'Rafzaqu'. It should be noted that 'Pacific Royale' is a previous release from the same breeding program as the present cultivar, 'Pacific Majesty', and that 'Pacific Majesty' is most definitely an improvement over 'Pacific Royale', particularly in regard to fruit color. Distinct characteristics of 'Pacific Majesty' include the combination of very large fruit, light red color that darkens slightly in cold storage, firmness, long shelf life and high yield discussed herein.

BRIEF DESCRIPTION OF THE PHOTOGRAPHS

DETAILED DESCRIPTION

Figure 1:
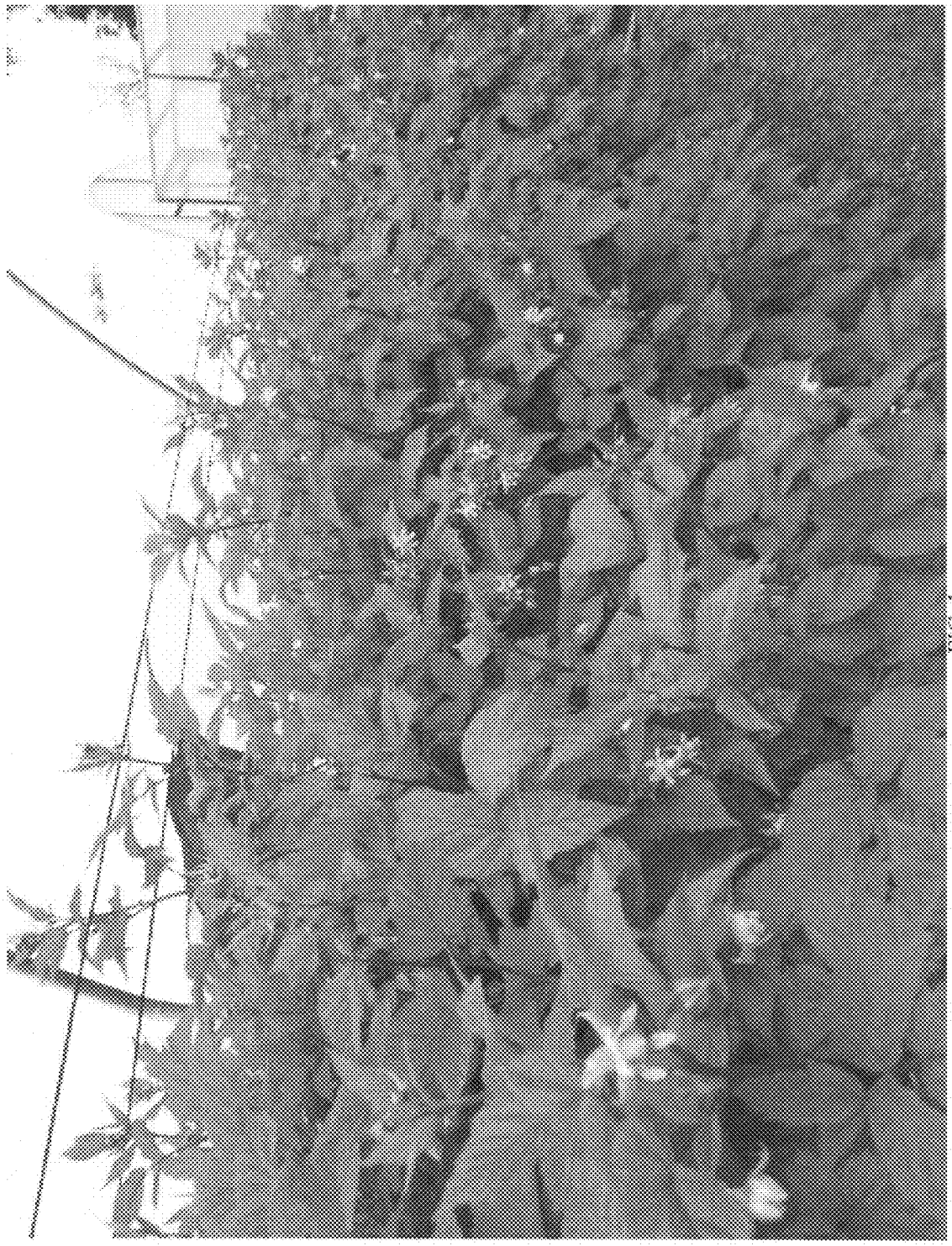
FIG. 1 is a photograph of the whole plant of the Raspberry cultivar 'Pacific Majesty' produced from root cuttings, showing floricanes aged 12 months.
Figure 2:
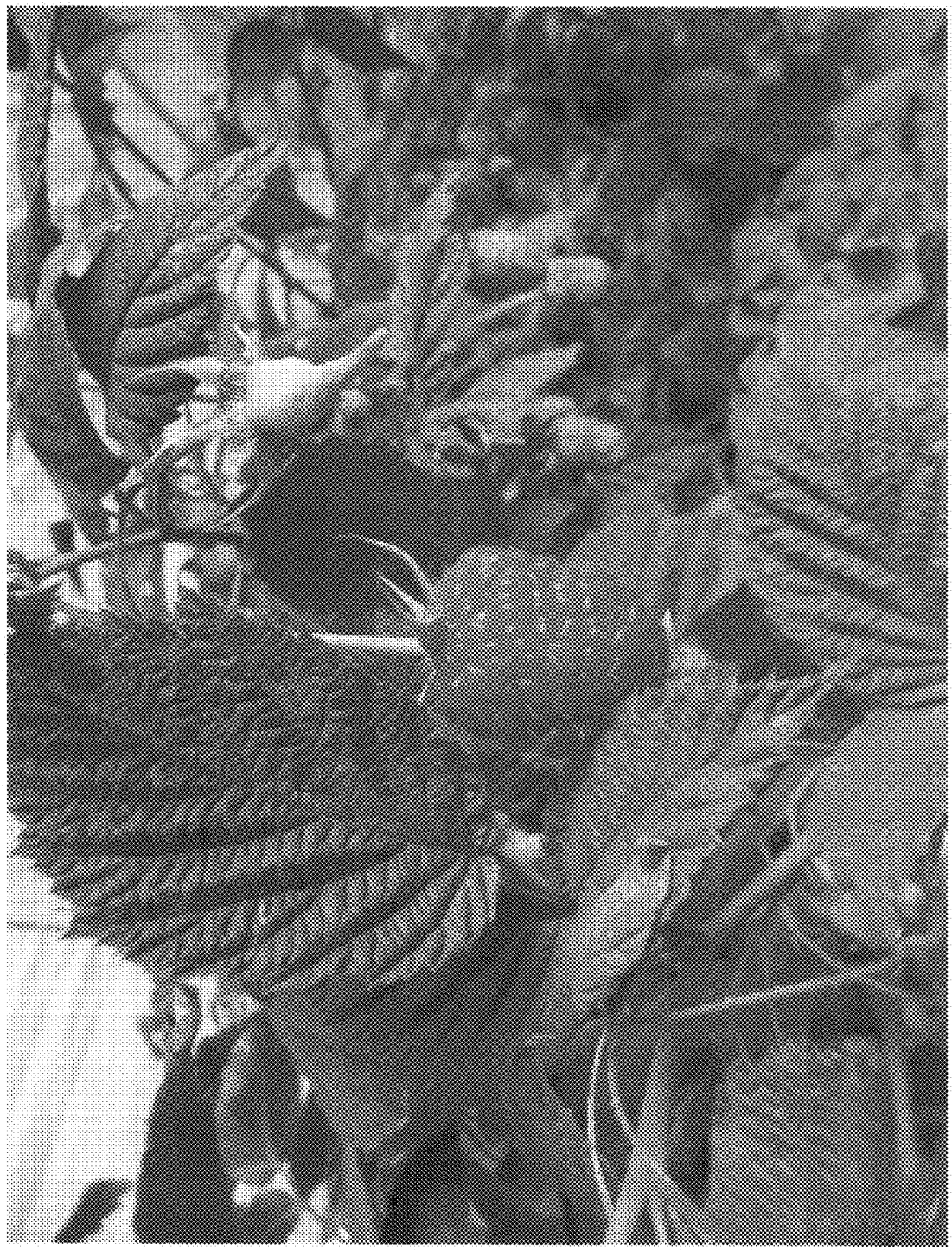
FIG. 2 is a photograph of primocane color and ripe fruit on primocanes of the Raspberry cultivar 'Pacific Majesty' produced from root cuttings, on primocanes aged 7 months.
Figure 3:
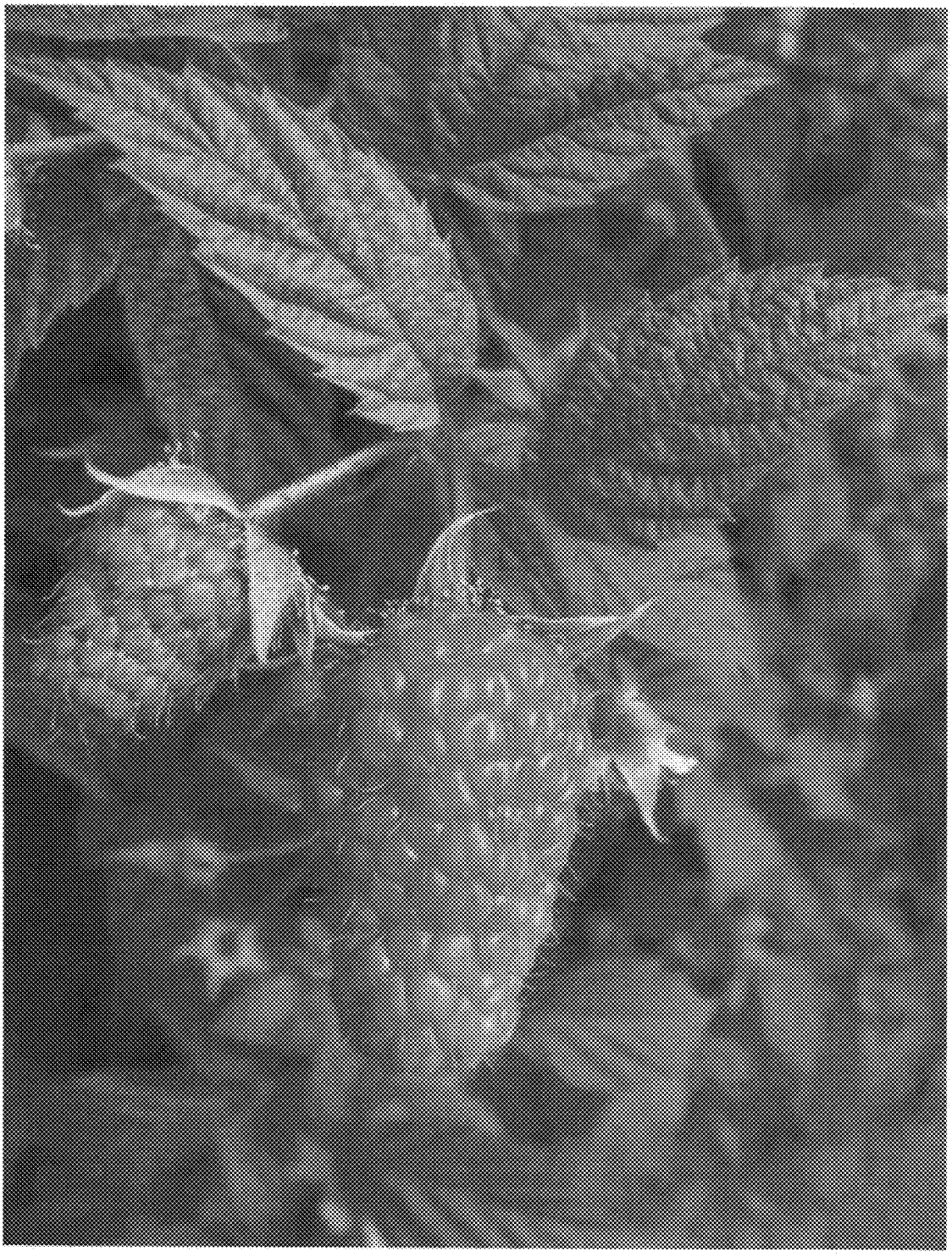
FIG. 3 is a close-up photograph of ripe and unripe fruit and leaf detail on floricanes of the Raspberry cultivar 'Pacific Majesty' produced from root cuttings, on primocanes aged 14 months.
Figure 4:
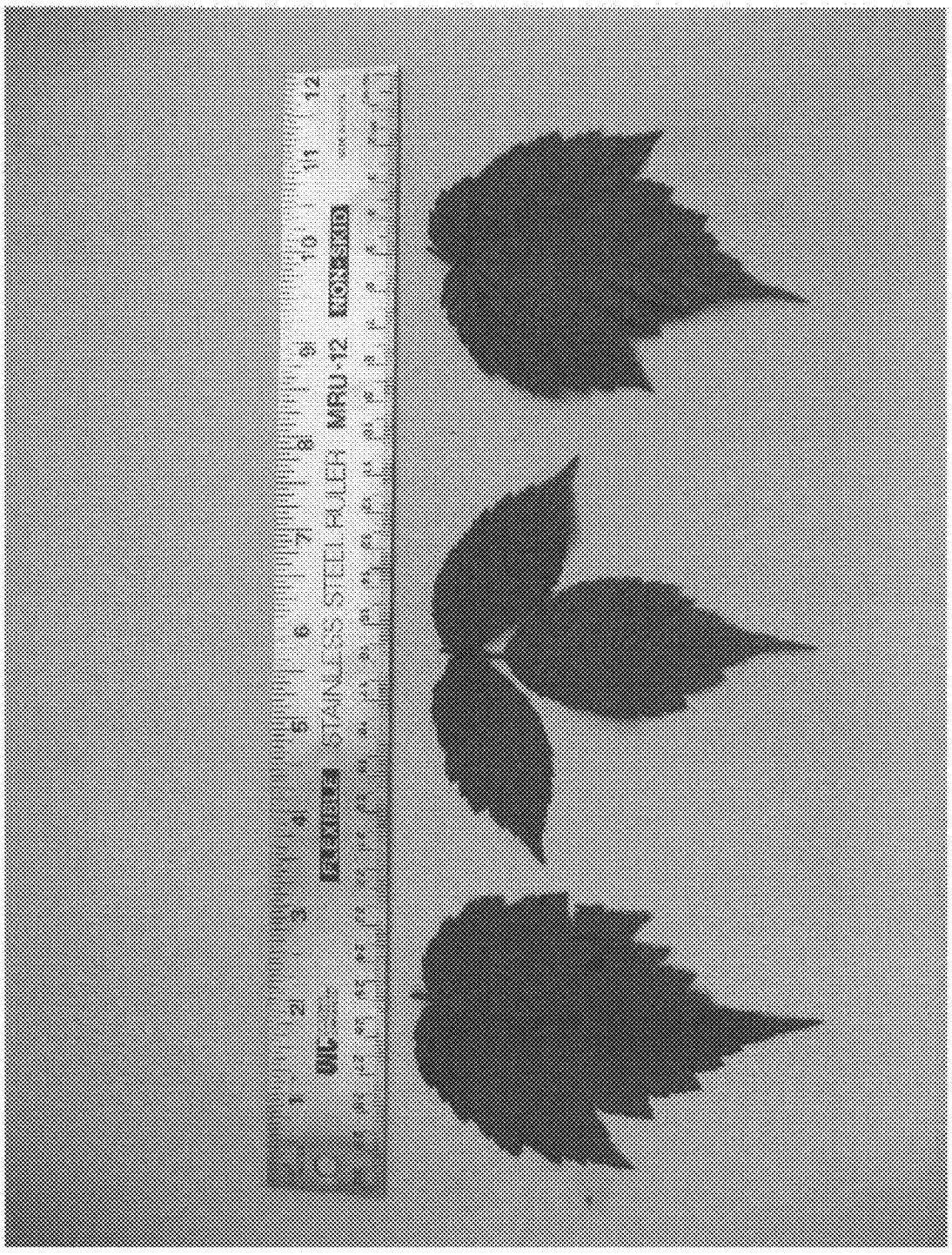
FIG. 4 is a photograph of the distinct leaf shape of the Raspberry cultivar 'Pacific Majesty' produced in vitro, aged 3.5 months.

Note: statements of characteristics herein represent exemplary observations of the cultivar herein and will vary depending on time of year, growing location, horticultural practices employed, annual weather, etc.

Cultivar name: 'Pacific Majesty'.

Classification:

*Family*.—Rosaceae.

*Botanical name*.—*Rubus idaeus*.

*Common name*.—Raspberry.

Parentage:

*Female parent* (*please provide name or code*).—Unknown.

*Male parent* (*please provide name or code flower*).—Unknown.

Pacific Majesty was first identified in a field with other seedlings in June 2007 at Watsonville, Calif. USA. The field of seedlings had been planted between 2004 and 2005, but it had been become overgrown and most of the tags that had marked the seedling populations had been lost. Thus, the parentage of Pacific Majesty is not known. Pacific Majesty was first propagated asexually by crown division in January 2008 in Watsonville, Calif. USA. The crown of the original plant was dug and parted into basal cane pieces (approximately 25 cm long) with root attached and replanted into a selection plot elsewhere on the farm, resulting in a 15-fold increase. Subsequent asexual propagation of Pacific Majesty was done in January 2009. Roots from the selection plot were dug, cold stored and then planted in a greenhouse in Watsonville, Calif. USA to force etiolated shoots, which were subsequently rooted and grown up to field-planting size. In May 2009, two actively growing primocanes of Pacific Majesty were dug (with root attached) from Watsonville, Calif. USA and shipped to Lafayette, Oreg. USA, where vegetative material was explanted and established in vitro for micropropagation.

Growing location for the observations herein: Watsonville, Calif. USA. The variety was also tested in Mexico and was found to be adapted to that climate.

Time of year (season): Autumn.

Age of plants used for this discussion: 7 months for primocanes; 12 months for floricanes.

Age of plants used for the photographs in the figures: 7 months, primocanes.

Type of greenhouse covering or growing structure, or field: High tunnel over field.

Light: Natural.

References to color refer to The R.H.S. Colour Chart—Fifth Edition.

Plant:

*Form/shape*.—Vase.

*Growth habit*.—Semi-Erect to Erect.

*Height*.—150 cm to 200 cm, as measured from crown to apex (primocanes).

*Spread*.—34 cm, on average, as measured from distal leaf tip to distal leaf tip.

*How propagated*.—Root cuttings, in vitro. As of the filing of the current application, at least 10 generations of Pacific Majesty (primarily in vitro) have been created and the characteristics herein have been stable.

*Time to initiate and develop roots*.—25 days from etiolated root cuttings.

*Root description*.—Fibrous.

Primocanes: (Note: Primocane data recorded on Oct. 21, 2010).

*Diameter*.—0.7 cm for a 1.6 m cane.

*Height*.—140 to 160 cm.

*Number of nodes*.—41 on average, for a 1.6 m cane.

*Internode length*.—3.7 cm on average.

*Number of canes/hill*.—10-12.

*Cane color*.—RHS 145A.

*Spine color*.—RHS 59A.

*Number of spines per unit area, the spine shape, spine length, spine width and spine apex descriptor*.—Spines/unit area: 3/cm$^2$. Spine shape: Acuminate. Spine length: 0.1 cm. Spine width: 0.01 cm. Spine apex descriptor: Acuminate.

Floricanes: (Note: Floricane data recorded on Apr. 2, 2011).

*Diameter*.—0.7 cm.

*Length*.—100 to 115 cm.

*Number of nodes*.—22 on average.

*Internode length*.—4.2 cm on average.

*Cane color*.—RHA 176A.

Leaves:

*Terminal leaflet*.—Size: Length: 10.5 cm (primocane). Width: 7.4 cm (primocane). Length/width ratio: 1.42. Shape of apex: Acuminate. Shape of base: Cordate. Margin: Doubly-serrate. Texture: Glabrous. Number of serrations/leaf: 128. Shape of serrations: Acuminate. Color: Upper surface: RHS N137A. Lower surface: RHS N138C. Venation pattern: Netted pinnate. Venation color: Upper surface: RHS N137B. Lower surface: RHS 145B. Shape of leaf in cross section: Odd pinnate; trifoliate and pentafoliate. Number of leaflets/leaf: 3 to 5. Interveinal blistering: No. Glossiness: Yes.

*Primocane leaves*.—Petiole length: 4.8 cm on average. Petiole diameter: 0.15 cm (primocane). Petiole color (upper): RHS 177A (primocane). Petiole color (lower): RHS 145B (primocane). Rachis length: 7.3 cm on average. 4 *Stipules/leaf:* 2 on average, if present. Stipule length: 0.6 cm. Stipule width: 0.08 cm. Stipule color: RHS 144A. Leaf color: Leaf Upper surface: RHS N137A. Leaf Lower surface: RHS N138C. Terminal leaflet: Length: 10.5 cm on average. Width: 7.4 cm on average. Petiolule length: 2.7 cm on average. Petiolule diameter: 0.09 cm. Petiolule color (upper): RHS 177A. Petiolule color (lower): RHS 145A. Distal lateral leaflet: Length: 5.9 cm on average. Width: 2.4 cm on average. Petiolule length: 0 cm (attached to rachis). Basal lateral leaflet: Length: 7.3 cm on average. Width: 4.9 cm on average. Petiolule length: 0 cm (attached to rachis).

*Floricane leaves*.—(Floricane data recorded on Apr. 2, 2011). Petiole length: 3.4 cm on average. Stipule length: 0.5 cm, when present. Color: Leaf Upper surface: RHS 144A. Leaf Lower surface: RHS 148B. Terminal leaflet: Length: 7.2 cm on average. Width: 5.8 cm on average. Petiolule length: 2.0 cm on average. Basal lateral leaflet: Length: 6.8 cm on average. Width: 3.3 cm on average. Petiolule length: 0 cm (attached to rachis).

Flowers:

*Time of flowering* (50% *of plants at first flower*).—10-June (primocanes, year one); 6-April (floricanes, year two).

*Size*.—Length: 0.9 cm on average. Diameter: 0.7 cm on average.

*Fragrance*.—None.

*Color*.—(Please see R.H.S. values for petal, stamen color).

*Peduncle*.—Length (cm): 1.3 cm on average. Diameter (cm): 0.7 cm on average. Color: RHS 139C. Pubescence: Present. Texture: Pubescent.

*Petal color*.—RHS 157A (both topside and underside).

*Petals/flower*.—5.

*Petal shape*.—Obtuse.

*Petal length*.—0.9 cm.

*Petal width*.—0.2 cm.

*Petal apex descriptor*.—Obtuse.

*Petal base descriptor*.—Obtuse.

*Petal margin descriptor*.—Entire, with some undulation near apex.

*Flowering trusses shape*.—Deltoid.

*Sepal*.—Quantity: 5. Length: 1.4 cm on average. Width: 0.3 cm on average. Color: Topside: RHS 147C; Underside: RHS 139C. Sepal apex descriptor: Acuminate. Sepal margin descriptor: Entire.

*Pedicel*.—Color: RHS 146B. Length: 5.9 cm per flower on average. Pedicel diameter: 0.05 cm.

*Receptacle color*.—RHS 159A.

Reproductive organs:

*Self fertile*.—Yes.

*Stamens*.—Number: 141 on average.

*Filament*.—Length: 0.3 cm on average. Diameter: 0.06 cm on average.

*Stamen color*.—RHS NN155B.

*Anthers*.—Color: RHS 197A. Length: 0.09 cm on average. Diameter: 0.02 cm on average.

*Pollen color*.—RHS 157D.

*Pollen amount*.—Sparse.

*Style*.—Length: 0.2 cm on average. Diameter: 0.01 cm on average. Color: RHS 157B.

*Stigma*.—Length: 0.01 cm on average. Diameter: 0.01 cm on average. Color: RHS 156B.

Fruit:

*Predominant shape*.—Conic.

*Weight* (*g*).—5.1-5.4 g, on average.

*Size*.—Length (cm): 3.4 cm, on average. Width (cm): 1.9 cm, on average. Length/width ratio: 1.63.

*Receptacle*.—Diameter: 1.0 cm, on average. Length: 2.0 cm, on average.

*Drupelet*.—Diameter: 0.4 cm, on average. Width: 0.3 cm, on average. Number: 134 to 156. Weight: 0.02 g, on average.

*Color of mature fruit*.—External: RHS 42B. Internal: RHS 48B.

*Firmness of skin*.—Moderate.

*Firmness of flesh*.—Moderate in Watsonville, Calif., USA to Firm in Zapotiltic, Jalisco, Mexico.

*Hollow center*.—Yes.

*Number of fruit per node*.—1 to 2.

*Time of ripening* (50% *of plants with first ripe fruit*).—20-May (floricanes); 25-July (primocanes, year one).

*Time of fruiting*.—Late spring, early summer (floricanes); Late summer, autumn (primocanes).

*Type of bearing*.—Primocane-fruiting.

*Exemplary fruit yield*.—16,307-18,200 lb/acre, on average.

*Berry brix*.—8.8.

Buds:

*Bud shape*.—Acute.

*Bud length*.—0.81 cm.

*Bud diameter* (*base*).—0.5 cm.

*Bud diameter* (*tip*).—0.1 cm.

*Bud color*.—RHS 144A.

Typical market use: Fresh.

Keeping quality: Very good.

Shipping quality: Moderate to Good.

Thus, in some general aspects, Pacific Majesty is a new and distinct variety of raspberry (*Rubus idaeus*) that can be identified, among other things, by its unique leaf appearance and hue, in particular the compound leaves on primocanes, which have a leaf color of N137A on the upper surface and N138C on the lower surface, and also due to the drupelets, which are typically uneven in size resulting in a slight curved conic form on nearly 100% of the fruit.

What is claimed is:

1. A new and distinct cultivar of Raspberry plant named 'Pacific Majesty' as described and shown herein.

* * * * *